United States Patent
Rothschild et al.

(10) Patent No.: US 7,955,855 B2
(45) Date of Patent: Jun. 7, 2011

(54) DETECTION OF MATERIALS VIA NITROGEN OXIDE

(75) Inventors: Mordechai Rothschild, Newton, MA (US); Charles M. Wynn, Groton, MA (US); John J. Zayhowski, Pepperell, MA (US); Roderick R. Kunz, Acton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 12/500,880

(22) Filed: Jul. 10, 2009

(65) Prior Publication Data
US 2010/0047916 A1     Feb. 25, 2010

Related U.S. Application Data

(60) Provisional application No. 61/080,028, filed on Jul. 11, 2008, provisional application No. 61/164,550, filed on Mar. 30, 2009.

(51) Int. Cl.
| | |
|---|---|
| *G01N 21/64* | (2006.01) |
| *G01N 21/00* | (2006.01) |
| *G01T 1/20* | (2006.01) |
| *G21G 4/00* | (2006.01) |

(52) U.S. Cl. ..... 436/89; 436/110; 436/116; 250/363.01; 250/493.1

(58) Field of Classification Search .................. 436/116, 436/98, 110; 250/363.01, 493.1
See application file for complete search history.

(56) References Cited

U.S. PATENT DOCUMENTS

| | | | |
|---|---|---|---|
| 5,364,795 | A | 11/1994 | Sousa et al. |
| 5,728,584 | A | 3/1998 | Sousa et al. |
| 5,751,472 | A | 5/1998 | Jeys et al. |
| 5,759,859 | A | 6/1998 | Sousa |
| 6,215,580 | B1 | 4/2001 | Kouta |
| 2007/0221863 | A1 | 9/2007 | Zipf |

OTHER PUBLICATIONS

Westblom U. et al., Detection of nitrogen atoms in flames using two-photon laser induced fluorescence and investigations of photochemical effects, Applied Optics, Jul. 20, 1991, vol. 30, No. 21, pp. 2990-3002.*

Arusi-Parpar, T. et al., "Photodissociation followed by laser-induced fluorescence at atmospheric pressure and 24° C.: a unique scheme for remote detection of explosives," Applied optics 40(36):6677-81 (2001).

(Continued)

*Primary Examiner* — Walter D Griffin
*Assistant Examiner* — Christine T Mui
(74) *Attorney, Agent, or Firm* — Thomas J. Engellenner; Giordana M. Belenchia-Sauer; Nutter McClennen & Fish LLP

(57) ABSTRACT

Methods and devices for detecting the presence of a NO forming material (e.g., a material that can form, or is, a nitrogen monoxide molecule) are disclosed based on detection of fluorescence exhibited by NO molecules in a first vibrationally excited state of a ground electronic state. Such excited NO molecules can be formed, for example, when small amounts of explosives are photodissociated. By inducing fluorescence of the material, a distinct signature of the explosive can be detected. Such techniques can be performed quickly and with a significant standoff distance, which can add to the invention's utility. In another aspect of the invention, methods and apparatus for generating electromagnetic radiation are disclosed. Such methods and apparatus can be used in conjunction with any detection method disclosed herein.

17 Claims, 11 Drawing Sheets

OTHER PUBLICATIONS

Arusi-Parpar, T. et al., "Remote detection of explosives by enhanced pulsed laser photodissociation/laser-induced fluorescence method," Stand-off Detection of Suicide Bombers and Mobile Subjects 59-68 (2006).

Cabalo, J. et al., "Detection of Hexahydro-1,3,5-trinitro-1,3,5-triazine (RDX) by Laser Surface Photfragmentation-fragment Detection Spectroscopy," Appl. Spectroscopy 57:1196-99 (2003).

Cabalo, J. et al., "Trace detection of explisoives with low vapor emissions by laser surface photfragmentation-fragment detection spectroscopy with an improved ionization probe," Appl. Optics 44:1084-91 (2005).

Guo, Y.Q., :"Decomposition of nitramine energetic materials in excited electronic states: RDX and HMX," J. Chem. Phys. 122:244310 (2005).

Heflinger, D. et al., "Application of a unique scheme for remote detection of explosives," Optics Communication 204:327-31 (2002).

Luque J. et al., "Transition probabilities and electronic transition moments of the $A^2\Sigma^+-x^2\Pi$ and $D^2\Sigma-x^2\Pi$ systems of nitric oxide," J. Chem. Phys. 111:7405 (1999).

"Optical Parametric Oscillator," Wikipedia, http://en.Wikipedia.org/wiki/Optical_parametric_oscillator.

Shu, J. et al., "The use of rovibrationally excited NO photofragments as trace nitrocompounds indicators," Appl. Phys. B 70:621-25 (2000).

Walsh, BM et al., "Compositionally tuned 0.94-um lasers: a comparative laser material study and demonstration of 100-mJ Q-switched lasing at 0.946 and 0.9441 um," IEEE J. Quantum Electronics 37(9):1203-09 (2001).

Wu D. et al., "2,4,6-Trinitrotoluene detection by laser-photofragmentation-laser-induced fluorescence," Appl. Optics 35:3998-4003 (1996).

Wynn, CM et al., "Experimental demonstration of remote optical detection of trace explosives," Proc of SPIE 6954:695407-1-8 (2008).

Wynn, CM et al., "Detection of condensed-phase explosives via laser-induced vaporization, photodissociation, and resonant excitation," Applied Optics 47(31):5767-76 (2008).

Wynn, C.M., DARPA program presentation, "Remote Detection of Explosives via UV Fluorescence," presented on Jul. 11, 2007.

Wynn C.M. et al., 2007 Scientific Conference on Chemical and Biological Defense Research, "Experimental Demonstration of Remote Optical Detection of Trace Explosives," presented on Nov. 15, 2007.

Wynn C.M. et al., SPIE presentation at Chemical Biological Radiological Nuclear Explosives (CBRNE) Sensing IX, "Experimental Demonstration of Remote Optical Detection of Trace Explosives," presented on Mar. 18, 2008.

* cited by examiner

DETECTION OF MATERIALS VIA NITROGEN OXIDE

CROSS REFERENCE TO RELATED APPLICATIONS

The present application claims the benefit of (i) a U.S. Provisional Patent Application bearing Ser. No. 61/080,028, entitled "Detection of Nitro-Bearing Materials," filed on Jul. 11, 2008; and (ii) a U.S. Provisional Patent Application bearing Ser. No. 61/164,550, entitled "Detection of Nitro-Bearing Materials," filed on Mar. 30, 2009. Both of these provisional applications are hereby incorporated herein by reference in their entirety.

STATEMENT REGARDING FEDERALLY SPONSORED RESEARCH OR DEVELOPMENT

This invention was made with U.S. government support under Air Force Contract Number FA8721-05-C-0002. The government has certain rights in the invention.

FIELD OF THE APPLICATION

The present application relates to devices and methods for detecting materials, particularly as directed to detecting nitro-bearing compounds, and other compounds, that may be present in materials such as explosives.

BACKGROUND

In numerous situations, when explosive devices are prepared, transported, or otherwise handled, small amounts (e.g., on the order of micrograms/$cm^2$) of the explosive material, or related residues, can become disposed on surfaces. Such surfaces may include clothing, a container, a vehicle, the ground, window sills, and other substrates. Detection of such chemicals can provide a warning of possible concealed assembly and/or transport of explosive materials and devices.

While several methodologies have been developed to detect such materials, each suffers from deficiencies and/or disadvantages. For instance, x-ray transmission, x-ray backscatter, terahertz (THz) imaging and the like are sensitive only to bulk amounts of explosive material or metallic constituents in explosive devices; such techniques typically cannot detect very low surface quantities of explosive materials/residues. Ion-mobility spectrometry (IMS) requires surface sampling, for instance by airflow agitation, followed by collection of dislodged particles. Thus, the detection is relatively slow, and effective only at short distances (e.g., 1-2 meters). Raman spectroscopy has a very weak signature, requiring data collection for extended periods of time. Laser-induced breakdown spectroscopy (LIBS) is prone to generating false alarms in many situations since it is largely non-specific, detecting atomic constituents which are found in many compounds (oxygen and nitrogen). Differential reflectometry is effective only from relatively short distances (~1 meter), and is also prone to generating false alarms since its signature is complex and not well defined. Fluorescence quenching (e.g., using the Fido™ detector by ICx Nomadics) has some of the drawbacks of IMS, requiring that target molecules reach the detecting device to interact with the fluorescing polymer. It is therefore limited to stand-off distances of ~1-2 meters.

Accordingly, a need persists for developing detection techniques, methods and associated devices, that can quickly and accurately detect trace amounts of explosives. Furthermore, it would be advantageous to perform such detection in a fast and efficient manner (e.g., by scanning moving vehicles or cargo without the need for surface sampling or manual handling of a sample).

SUMMARY

Methods and devices for detecting the presence of a substance such as a NO-bearing material (e.g., a material having a portion including a nitrogen atom and oxygen atom bonded together) are disclosed based on detection of fluorescence exhibited by portions of such a material in a first vibrationally excited state of a ground electronic state. Excited NO molecules can be formed, for example, when small amounts of substances such as explosives (e.g., DNT, TNT, PETN, RDX, and HMX) or other materials associated with explosives (e.g., urea nitrate) are photodissociated. By inducing fluorescence of NO molecule, a distinct signature of the substance (e.g., explosive) can be detected. In particular, the fluorescence signature can be distinct from fluorescence induced, if any, in molecules derived from benign NO-containing components typically found in the environment (e.g., atmospheric components or fertilizer), allowing for low false alarms. Such a technique can be performed quickly and with a significant standoff distance, which can add to the invention's utility.

Some exemplary embodiments are drawn to methods for identifying the presence of a substance such as a parent molecule, which can be associated with an explosive compound (e.g., 2,6-dinitrotoluene, 2,4,6 trinitrotoluene, pentaerythritol tetranitrate, hexahydro-1,3,5-trinitro-1,3,5-triazine, and cyclotrimethylenetrinitramine). Another substance that can be identified is urea nitrate, which can be found in fertilizer-based high explosives. The substance can be present in an unknown sample (e.g., material disposed on a substrate surface in a solid form), which is to be identified. The sample can be photodissociated into one or more portions that include NO, wherein the NO includes an electron disposed in a first-vibrational excited state of an electronic ground state. Vaporization of the sample and/or fragments can also be performed while performing photodissociation, or by using a separate step. Laser induced fluorescence can be employed to induce fluorescence of the NO. Subsequently, the fluorescence of the NO can be detected (e.g., looking for radiation with a wavelength of about 226 nm) to thereby identify the presence of the molecule. The identification can include distinguishing the substance (e.g., parent molecule) from one or more other types of materials having a NO portion (e.g., an atmospheric NO-containing compound, an inorganic NO-containing compound, and fertilizer).

In some embodiments, the steps of photo-dissociating and employing laser induced fluorescence can be performed using the same excitation wavelengths, or performed as separate steps (e.g., using different wavelengths of radiation). In some embodiments, the laser-induced fluorescence includes exciting an electron using a wavelength of about 236.2 nm. In particular embodiments, the step of photodissociating can include photodissociating the sample into NO molecules, each having an electron in a first-vibrational excited state and having a distinct rotational state. As well, the step of employing laser-induced fluorescence can include inducing fluorescence of the NO in distinct rotational states (e.g., by fluorescing using a plurality of excitation wavelengths centered around 236.2 nm and having a bandwidth from about 0.2 nm to about 2 nm). In some embodiments, the method can be carried out in a stand-off mode (e.g., using a detector positioned at least about 50 cm, and/or less than about 150 meters, from the sample). Some embodiments perform the method in ambient conditions (e.g., photodissociating and fluorescing in air at typical indoor and/or environmental conditions).

In another aspect of the invention, methods and apparatus for generating electromagnetic radiation are disclosed. Such methods and apparatus can be used in conjunction with any detection method disclosed herein or with a system to detect substances. The apparatus includes an electromagnetic source configured to generate radiation with a selected profile. The selected profile can have a center wavelength at about 236.2 nm, and can have a bandwidth between about 0.2 nm and about 2 nm. A spectral filter can be optically coupled to the apparatus, and can be configured to filter at least one wavelength outside the selected profile.

In some instances, the electromagnetic source can be configured to produce a pulsed electromagnetic output. One or more of the pulses can be characterized by a repetition rate greater than about 1 kHz, and/or a pulse length less than about 10 nsec or less than about 2 nsec.

In some embodiments, the electromagnetic source can include an optical source for producing an electromagnetic output. The electromagnetic output characterized by a wavelength center being an integer multiple of about 236.2 nm. The electromagnetic output can also have a bandwidth consistent with allowing the electromagnetic source to generate a centered 236.2 nm output with a bandwidth between about 0.2 nm and about 2 nm. The electromagnetic source can also include one or more harmonic converters to convert the electromagnetic output into radiation centered at about 236.2 nm. A harmonic converter can include a lithium-based crystal and/or a barium-based crystal. One or more amplifiers can also be included for increasing power of the electromagnetic radiation to provide a selected minimum target energy density. An amplifier can include a Nd-doped mixed garnet configured to increase the power of electromagnetic radiation having a wavelength of about 944.8 nm.

In some particular embodiments, the optical source can be an amplified time-gated superluminescent diode or other type of amplified spontaneous emission source. In other embodiments, the optical source can include a pulsed laser. The optical source can also include an optical parametric generator configured to be pumped by the pulsed laser, or one of its harmonics, to produce the electromagnetic output. Non-limiting examples of pulsed lasers can include a Q-switched laser, a cavity-dumped laser, a gain-switched laser, an amplified time-gated continuous wave laser, and a gated long-pulse laser. In one example, the pulsed laser comprises a passively Q-switched Nd:YAG laser. In some instances, the optical parametric generator includes a periodically poled material, and is configured to produce the electromagnetic output with the wavelength center at about 1889 nm.

Other embodiments are directed to systems for remotely detecting the presence of a molecule such as used in an explosive. The system can include an electromagnetic source such as any of the versions described herein. A detector can be included to receive electromagnetic radiation from a fluorescing NO molecule. For example, the detector can be configured to detect electromagnetic radiation that includes a wavelength of about 226 nm. Such systems can be configured to provide standoff detection at a selected distance (e.g., at a distance greater than about 10 meters and/or less than about 150 meters).

BRIEF DESCRIPTION OF THE DRAWINGS

The present application will be more fully understood from the following detailed description taken in conjunction with the accompanying drawings (not necessarily drawn to scale), in which.

DETAILED DESCRIPTION

Figure 1:
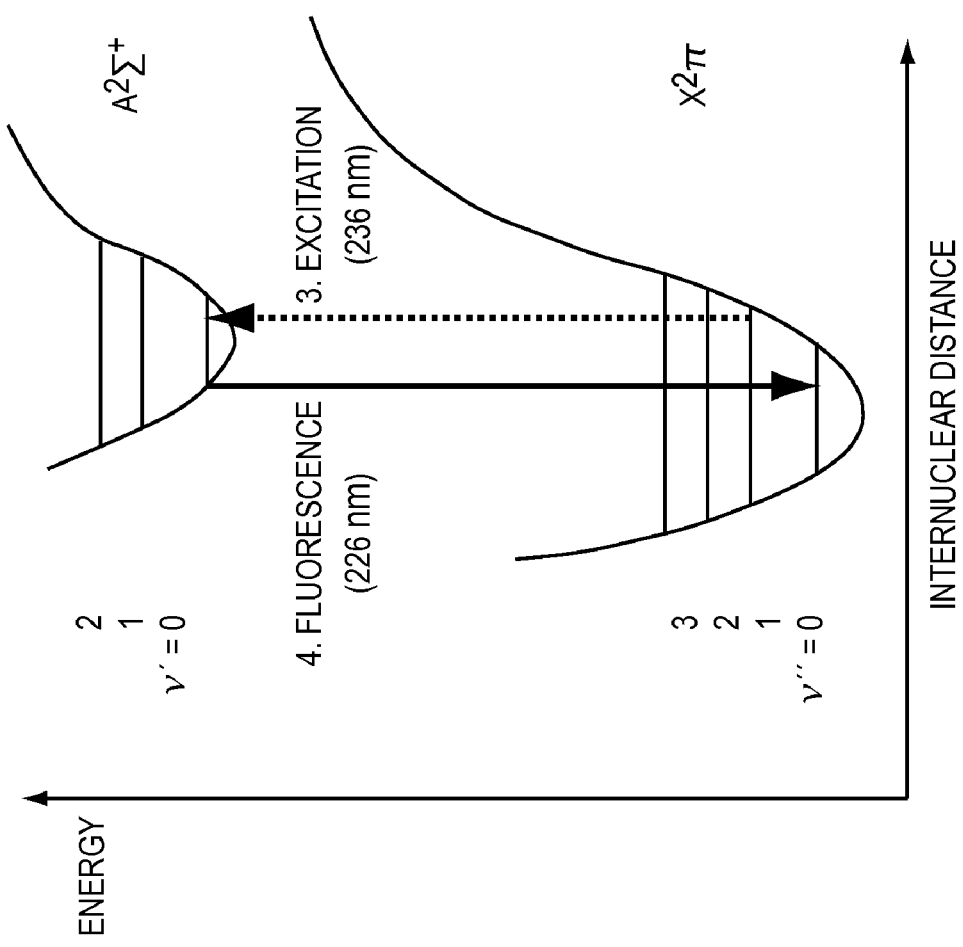
FIG. 1 depicts a schematic diagram of the excitation and fluorescence of an electron in a NO molecule from a first vibrational excited state of the electronic ground state, in accord with some embodiments of the invention.

Some embodiments are directed to identifying the presence (e.g., via remote detection) of a substance in a target (e.g., a molecule or fragments of the molecule) by detecting photons emitted therefrom. The terms "target" and "sample" are synonymous and refer to a material to be probed or detected. While numerous substances can be detected or identified by the techniques and devices discussed herein, in some embodiments, the substance comprises, or is transformed to form, a nitrogen monoxide molecule (herein a "NO molecule" or "NO fragment"). Thus, a substance whose presence is to be detected can be a NO-containing material (i.e., containing a portion that has a nitrogen atom bonded to an oxygen atom therein such as a nitro-containing material or a nitrate-containing material), and/or can be transformed to form one or more NO molecules that can act as a signature for the presence of the substance.

The phrases "remote detection" and "standoff detection" are synonymous and refer to detection of a substance without the need to utilize manual collection methods (e.g., surface collection and sample preparation) and/or manual sample concentration techniques; as well, the detection can be performed at a distance. While standoff detection can be utilized at very close distances, e.g., within about 0.5 meters of a surface having a sample, in some embodiments the distance is much longer (e.g., greater than about 0.5, 1, 5, or 10 meters). In some embodiments, the standoff distance is shorter than about 150 meters or 100 meters. It is understood that the term "remote" and "standoff" can also be used to describe other processes such as irradiation, and can refer to any of the distance measures previously described.

Substances to be detected (e.g., explosives or other parent molecules) can be present on a variety of surfaces either as finely distributed molecules or aggregated in small particles. They can reside on larger particles such as dust; be intercalated in near-surface structures such as fibers of textile, loose paint, porous wood or concrete; or they may be present on solid surfaces such as metal, wood, plastic, glass, and so on. In all these forms, the substance is available for remote, non-contact detection according to some embodiments of the present invention.

In some embodiments, the sample to be probed can include a NO containing (e.g., nitro-bearing) molecule, where the molecule and/or fragments can be disposed to allow generation of a distinguishing signature for the sample. In some instances, these targets include explosive compositions. As utilized herein, the term "explosive" refers to a molecule of the explosive compound or a residue associated with the explosive. Examples of explosives that are potential targets include 2,6-dinitrotoluene (DNT), 2,4,6 trinitrotoluene (TNT), pentaerythritol tetranitrate (PETN), hexahydro-1,3,5-trinitro-1,3,5-triazine (HMX), and cyclotrimethylenetrinitramine (RDX). Other explosive molecules, including other explosives capable of forming NO molecules, can also be potentially identified.

Another example of a substance for detection is urea nitrate. Urea nitrate is a substance found in high explosives made from fertilizers, and can be formed by the nitration of urea using, for example, nitric acid. Urea nitrate can be transformed to form a NO fragment, like some of the aforementioned explosives, which is susceptible to detection by some of the embodiments described herein. As well, some embodiments of the invention can distinguish the presence of urea nitrate from urea. While urea nitrate is an uncommon compound in the environment, urea is much more prevalent. Accordingly, such embodiments can decrease the false positives related to urea nitrate detection relative to other conventional techniques.

It is understood, however, that the signatures discussed herein can be used to identify the presence of particular NO-containing molecules that are not explosive compositions. As well, it is understood that while many embodiments herein discuss the detection of a NO molecule, the fluorescence signature discussed herein can also potentially be used to detect actual molecules. Accordingly, alternative embodiments of the invention can modify embodiments regarding explosives detection and NO-containing molecule detection to detect non-explosive compositions and/or NO-containing molecules.

In some embodiments, NO molecules and/or vaporization of a sample can be generated by remote irradiation of a sample on a surface of interest. In instances where the sample to be examined contains molecules that are typically non-fluorescing, the conversion of the molecule (e.g., associated with an explosive) present on a surface to a fluorescing species, and detection of the resulting fluorescence, can take place in a non-contact, remote fashion from the surface. It can also occur substantially instantaneously, e.g., within 100 nsec or less.

In some embodiments, detection of a target relies upon detecting fluorescence due to an electron moving from a first vibrational state ($v''=1$) of the electronic ground state ($X^2\Pi$) of the target. Using techniques discussed herein, the electron in the first vibrational state can be excited to the vibrational ground state ($v'=0$) of the first electronically excited state ($A^2\Sigma^+$) (e.g., using radiation at about 236.2 nm), resulting in a fluorescence when the electron relaxes to the vibrational ground state ($v''=0$) of the electronic ground state. This is shown diagrammatically in FIG. 1. The product radiation of the fluorescence (e.g., at about 226 nm) can be detected remotely, and can serve as a distinct signature of the target (e.g., a NO-containing material).

Accordingly, some embodiments of the invention can provide substantial advantages over other systems and methods of detecting substances such as explosives. For example, the detection can be non-contacting, relying on lasers irradiating the surface and on remote detection of photons. Accordingly, systems and methods capable of stand-off distances of 10-100 meters, for example, are possible using appropriate laser energy and efficiencies in the fluorescence detection system. At such distances, very small amounts of explosive materials (e.g., between about 0.1 and about 10 µg) can be detected. As well, detection can be conducted quickly as it occurs within or shortly after the excitation (e.g., within ~100 nsec). Detection techniques in accord with some embodiments can also exhibit a very low rate of false alarm rate. For instance, very few materials except for NO-bearing targets having electrons in a $v''=1$ state are expected to fluoresce at 226 nm following excitation at the longer 236.2 nm wavelength. Many materials do fluoresce at wavelengths longer than those at which they are excited, but not many at shorter wavelengths, and very rarely at the same 226 nm as NO.

Methods of Interrogating an Unknown Sample for a Substance

Some embodiments of the present invention are drawn to methods of interrogating an unknown sample for a substance (e.g., a NO-containing target) by detecting an electron in a first vibrational excited state of an electronic ground state of a molecule. For instance, particular embodiments are drawn to determining whether the a substance is present in an unknown sample, such as an explosives related composition (e.g., DNT, TNT, PETN, HMX, RDX, and/or urea nitrate). Photo-induced dissociation of the sample (e.g., a solid material, which can be disposed on a surface) can be performed so that at least one of the fragments of the sample includes a NO complex in the first vibrational state ($v''=1$) of its electronic ground state ($X^2\Pi$); vaporization of the sample molecules residing at or near the surface can also be performed substantially simultaneously, or through a separate step. Laser induced fluorescence can be employed to induce fluorescence of the NO complex from the first vibrational state. For example, excitation of the vibrationally excited NO can be performed to the vibrational ground state ($v''=0$) of the first electronically excited state ($A^2\Sigma^+$), followed by fluorescence from the electronically excited state to the vibrational ground state ($v''=0$) of the electronic ground state ($X^2\Pi$). The fluorescence can then be detected, which can thereby act as an identification of the presence of the molecule.

The step of vaporization can be induced remotely by a radiation source causing local heating, such as a laser whose radiation is absorbed by the explosives molecule and/or the surface to which it adheres. The vaporization steps can be accomplished with lasers operating at a variety of wavelengths because the target molecules exhibit broad spectral absorption features. For instance, an infrared laser such as a $CO_2$ laser operating near 10.6 μm wavelength can perform this function. Alternatively, an ultraviolet laser, for instance, conveniently operating near 355 nm, 266 nm, or some other UV wavelength can do the same. For example, TNT molecules are known to absorb ultraviolet radiation over a broad range of wavelengths, extending from. about 400 nm to about 190 nm and below. Therefore, a laser operating in this wavelength range can be absorbed by the molecule, causing it to heat up and turn from solid into vapor. This function can be accomplished with a continuous-wave or pulsed laser, with average power levels from milliwatts (mW) to watts (W) or pulse energy from microjoules (μJ) to Joules (J), depending on the absorptive properties and the thermal properties of the explosive molecules and the substrate the molecule resides on.

Photo-induced dissociation can be induced after vaporization. Like vaporization, the photodissociation can be accomplished with lasers operating at a variety of wavelengths, e.g., in the ultraviolet. In some instances, the vapor molecules can be dissociated by the ultraviolet wavelength at which the molecule absorbs such as sub-400 nm for TNT. Furthermore, the steps of vaporization and photo-induced dissociation can be induced by the same (e.g., ultraviolet) laser, in which case the distinction between the two steps is blurred. In some embodiments, photo-induced dissociation can occur first, while the explosive molecule is still in solid phase, with the fragments becoming volatile. In either situation, UV irradiation can result in fragments with a NO molecule being formed in a volatile state.

As a result of the photodissociation, a fraction of the NO fragments can be formed in the vibrationally excited state ($v''=1$) of the NO electronic ground state. This is a unique feature of the organo-nitrate explosive compounds, and has not been reported for other non-explosive nitro-bearing compounds or nitrates. Indeed, as will be described in the Examples, we have experimentally validated this assertion for several commonly found non-explosive nitrates and nitrites. These other compounds, upon ultraviolet-induced dissociation, form primarily NO in its vibrational ground state ($v''=0$). This unique property of explosives (the formation of NO in $v''=1$) is one reason for a very small level of false alarms according to some embodiments of the present invention. Accordingly, the identification of the molecule of interest can be distinguished from one or more other types of NO-containing materials such as atmospheric NO-containing compounds, inorganic NO-containing compounds and/or nitrates, and/or fertilizer.

In some embodiments, photo-induced excitation to the electronic A state utilizes a selected wavelength or range of wavelengths. For example, a preferred wavelength can be at about 236.2 nm (in air). Effective excitation of the NO photofragments can occur when such fragments are irradiated at this wavelength with short pulses (e.g., about 0.1 to about 10 nsec). The energy density per pulse of the radiation at the surface can be in a range between about 0.01 mJ/cm$^2$ and about 100 mJ/cm$^2$. Accordingly, in some embodiments, the functions of vaporization, dissociation, and excitation can be accomplished with one laser and substantially within one laser pulse. Alternatively, the three steps can be accomplished with two or more different lasers, each selected to perform a function corresponding with one or more of the steps.

Figure 2:
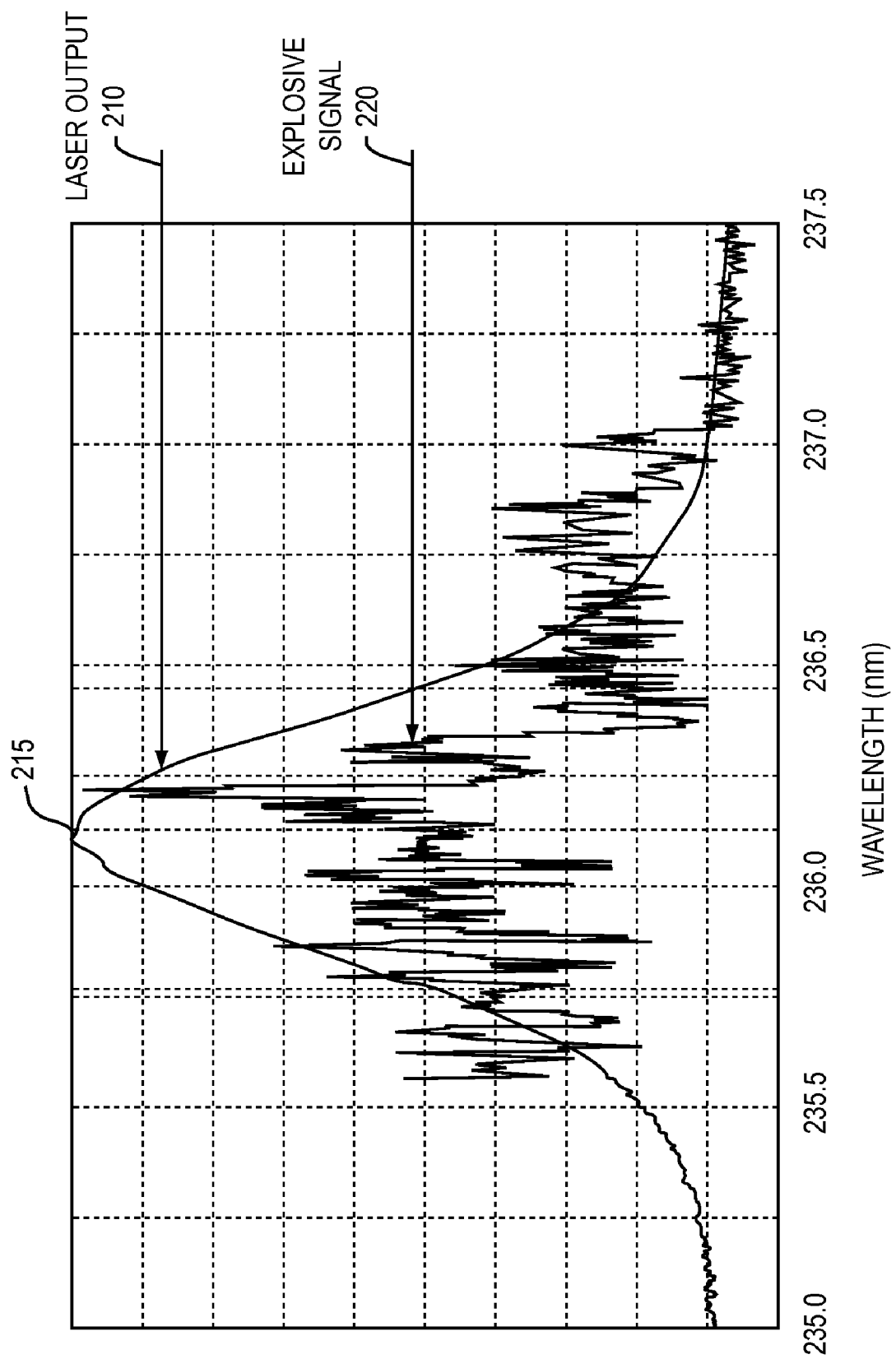
FIG. 2 presents an overlay of (i) a fluorescence signal from a NO molecule as a function of excitation wavelength, and (ii) a spectrum of an electromagnetic source as a function of wavelength, in accord with embodiments of the invention.

As shown in FIG. 2, and discussed more in depth in the Examples, photodissociated samples can exhibit a range of wavelengths at which they are excited from the first vibrationally excited state of the ground state. The range can be centered around about 236.2 nm, and can have a spread in the range of a few nanometers. Without necessarily being bound by any particular theory, it is believed that such a spread can be due to the rotational energy distribution of the excited electrons in the $v''=1$ state. Since the photodissociation of a sample can result in such a distribution of NO fragments, some embodiments can employ laser induced fluorescence over a range of wavelengths (e.g., about 0.2 nm to about 1 nm or 2 nm) to excite fragments in different rotational states. For instance, as shown in FIG. 2, a electromagnetic source can be configured to have a spread of wavelengths 210 around a center point 215 (e.g., 236.2 nm) which can capture a substantial portion of the rotational states 220. Such a spread in excitation wavelength can be advantageous by boosting the population of fragments to be fluoresced (e.g., by a factor of about 10) and enhancing the fluorescence signal to be detected.

The resultant fluorescence step of the NO photofragment can occur at a wavelength of approximately 226 nm, and can occur within less than about 100 nsec from the moment of photo-excitation. This fluorescing wavelength has been calculated from known spectroscopic constants of NO, and also has been validated in our experiments. The lag between excitation and emission is calculated from the known radiative lifetime of the NO excited state, and also taking into account that this lifetime is shortened due to collisions with other molecules present in air at normal atmospheric pressures.

Embodiments consistent with some of the previously described methods can result in highly sensitive detection with relatively low false alarm rates. As documented in the Examples, the spectral response near 236.2 nm has been well characterized, and it is possible that features of this relatively unusual spectrum could be used to aid in sensitivity or in reducing false alarms.

Systems and Devices for Detecting NO-Containing Targets

Some embodiments of the present invention are directed to systems for remotely detecting the presence of selected molecules, such as explosives and signatures of their presence. Such systems can include an electromagnetic source capable of inducing fluorescence of a NO-containing material having electrons in the first vibrational state of the electronic ground state of the NO group, and a detector configured to detect the fluorescence. The system can be configured to detect the fluorescence at a distance of greater than about 0.5, 1, 5, or 10 meters. In some embodiments, the standoff distance can be shorter than about 150 meters or 100 meters. As well, the system can be configured to detect small amounts of molecules on surfaces (e.g., in the microgram or submicrogram range such as less than about 100, 50, 40, 30, 20, 10, 1, or 0.1 micrograms). It is understood that systems consistent with embodiments can incorporate any of the features disclosed herein, including features associated with the methods herein, in any appropriate combination without limitation.

Some particular embodiments are drawn toward an apparatus that generates electromagnetic radiation, which can be incorporated in a detection system as disclosed herein. The apparatus can include an electromagnetic source configured to generate radiation with a selected profile. The profile, which can be relatively featureless, can have a center wavelength of about 236.2 nm. The profile can also be characterized by a bandwidth capable of exciting at least a portion of the electrons distributed in distinct rotational states of a first-vibrationally excited ground electronic state of a NO-containing material (e.g., explosive material as described herein). For example, the bandwidth can be between about 0.2 nm and about 1 nm or about 2 nm; or can be around 0.5 nm. As utilized herein, the term "bandwidth" can refer to a measure of the wavelength spread in the radiation emitted from a source. Such measures include those known to one skilled in the art. (e.g., the bandwidth can refer to the full width of the spectra at half maximum). Such a spread can be advantageous in exciting a population of NO fragments in different rotational states, which can thereby enhance a potential fluorescing signal. It is understood that other embodiments can alter the profile of such a source.

The electromagnetic source can optionally incorporate other features as well. For example, the electromagnetic source can act as a pulsed source. The pulses can be characterized as having a repetition rate greater than about 1 kHz (e.g., being in a range from about 1 kHz to about 5 kHz). The pulses can be also be characterized by a pulse length of less than about 10 nsec, for example, a length less than about 2 nsec, the latter being the lifetime of an intermediate state in the excitation process. It can also be desirable that the pulses exhibit an energy density at the target of at least about 5 mJ/cm$^2$ which can be at the level to photolyze a 1 cm$^2$ monolayer of explosive residue. It should be also understood that pulse duration and optical bandwidth can be traded off against the efficiency of the detection system. Thus, slight increases in the pulse duration and/or decreases in the bandwidth can be utilized. Accordingly, variations in these parameters are within the scope of the present application. Spectral filtering can also be incorporated to limit the bandwidth of the 236.2-nm output to the width selected. It can be preferable, but not necessary, to have the spectral filter before most of the optical amplification to improve the efficiency of the system.

Accordingly, some embodiments utilize an electromagnetic source that can include an optical source for producing an electromagnetic output characterized by a wavelength center being an integer multiple of a selected wavelength (e.g., about 236.2 nm). The output of the optical source can provide a selected bandwidth spread such that the electromagnetic source is able to provide the selected profile. One or more harmonic converters can also be included to convert the electromagnetic output of the optical source into electromagnetic radiation centered at the selected wavelength (e.g., about 236.2 nm). As well, one or more amplifiers can be utilized for increasing the power of the electromagnetic source such that the electromagnetic source can provide a selected minimum target energy density, which can be sufficient for standoff detection. For close range operations, the energy density at the target can be as low as about 0.05 mJ/cm$^2$ while longer standoffs can utilize an energy density greater than about 5 mJ/cm$^2$.

For instance, an electromagnetic source can include a Q-switched laser and an optical parametric generator (OPG). The Q-switched laser can produces pulses with a duration of less than about 2 nsec, and sufficient peak power (e.g., possibly with the assistance of an optical amplifier) to pump the OPG. The OPG, pumped by the Q-switched laser or one of its harmonics, can operate at a wavelength that is an integer multiple of 236.2 nm. The OPG can have sufficient bandwidth to generate the desired bandwidth (e.g., ~0.5 nm) at 236.2 nm after harmonic conversion. One or more stages of harmonic conversion can be included to convert the output of the OPG to light having a wavelength of about 236.2 nm. Amplification can be provided at any point in the optical train to provide adequate pulse energy at 236.2 nm. Because of the inefficiencies inherent in nonlinear optical processes, and the complications introduced by excessively high peak optical power, it can be desirable to have the amplification as late in the optical train as possible.

Figure 3:
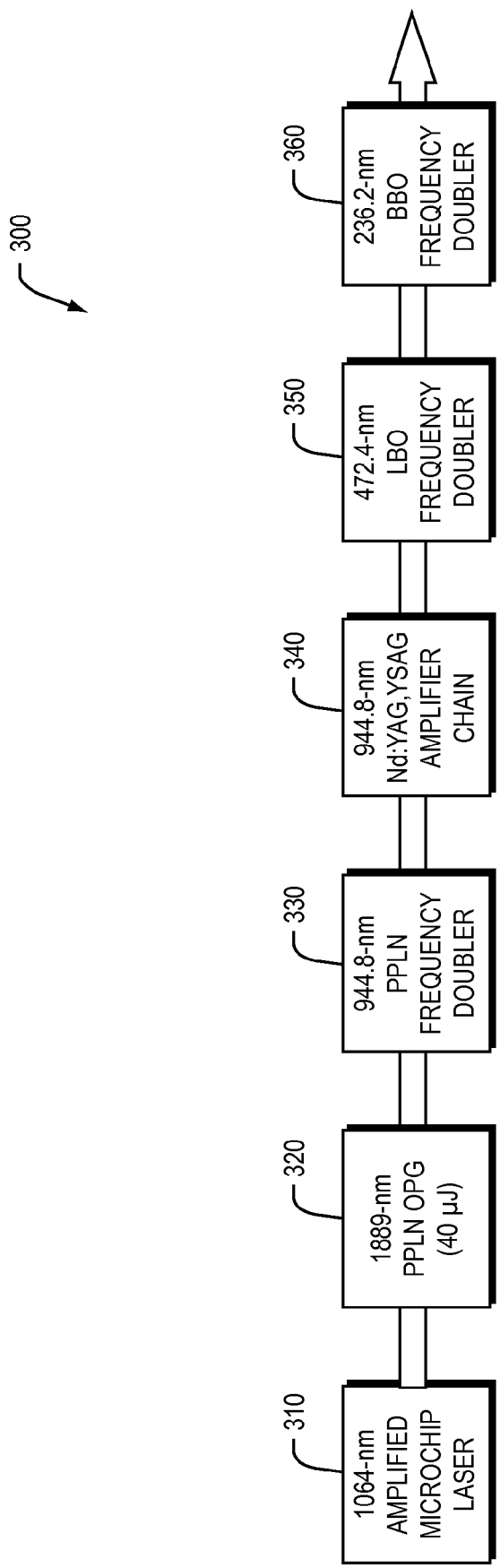
FIG. 3 presents a schematic diagram for an electromagnetic source, consistent with some embodiments of the invention.

Some particular embodiments of an electromagnetic source are consistent with the optical train 300 depicted in FIG. 3. The electromagnetic source can include a passively Q-switched neodymium doped yttrium aluminum garnet (Nd:YAG) microchip laser 310 operating at a wavelength of about 1064 nm, with a Nd:YAG amplifier to bring the pulse energy to about 100 to about 200 µJ. A periodically poled lithium niobate (or alternatively, periodically poled lithium tantalite) OPG 320 operating at a center wavelength of 1889 nm, with a bandwidth of several nanometers, can be pumped by the output of the Nd:YAG microchip laser. A periodically poled lithium niobate (or periodically poled lithium tantalite) frequency doubler 330 can be used to convert the output of the OPG to a wavelength of 944.8 nm.

Amplification can be provided by a chain of optical amplifiers, which can utilize a compositionally tuned Nd garnet such as 1% Nd:YAG$_{0.45}$YSAG$_{0.55}$ (YSAG-yttrium scandium aluminum garnet) or another appropriate material 340, including the possibilities discussed in "Compositionally tuned 0.94-µm lasers: a comparative laser material study and demonstration of 100-mJ Q-switched lasing at 0.946 and 0.9441 µm," by B. M Walsh, N. P. Barnes, R. L. Hutcheson, and R. W. Equal, IEEE Journal of Quantum Electronics, Vol. 37, No. 9, September 2001, pg. 1203-1209 as the gain medium to amplify the light at 944.8 nm. The reference is hereby incorporated herein by reference in its entirety. In these embodiments, spectral filtering can be provided by the bandwidth of the optical amplifier chain. A lithium triborate frequency doubler 350 can be used to convert the output of the amplifier chain to a wavelength of ~472.4 nm, followed by a beta barium borate frequency doubler 360 to convert the wavelength to ~236.2 nm.

Alternatives to the specific electromagnetic source configurations herein can substitute an amplified time-gated superluminescent diode or other amplified spontaneous emission source for the combination of the Q-switched laser and OPG. In other alternatives, a cavity-dumped laser, a gain-switched laser, or an amplified time-gated continuous wave or long-pulse laser could be used in place of the Q-switched laser. Those skilled in the art will realize that the Q-switched laser, or its substitute, and the optical amplifiers can operate at a variety of wavelengths, using a variety of gain media; and that there are a variety of nonlinear optical materials that can be used for the OPG and the harmonic converters.

Returning to the discussion of remote detection systems, consistent with some embodiments of the present invention, any appropriate detector can be utilized to detect the fluorescence signal created by the electromagnetic source, including those known to one skilled in the art. In some embodiments, an ultrasensitive detector can be utilized. Non-limiting examples include a photon-counting photomultiplier or Geiger-mode avalanche photodiode element or array equipped with a wavelength-selective filter. The filter can be configured to transmit the fluorescent photons, but reject scattered laser light at 236.2 nm and/or any other fluorescence at other wavelengths due to photo-induced excitation of other species.

Other devices can be included with the remote detection systems disclosed herein. For example, hardware associated with pointing and tracking can be incorporated to scan a beam over a surface in a designated pattern. Other optical devices can be incorporated to further manipulate an excitation beam or collection of fluorescence. Hardware, which can separately induce photodissociation and/or vaporization of a sample, can also be included. As well, processors, including hardware and/or software, can be included to operate the various devices within the parameters necessary to perform the techniques disclosed herein. These variations and others, including those understood by one skilled in the art, can be included within the scope of the present invention.

Standoff Distance Calculations

Figure 4:
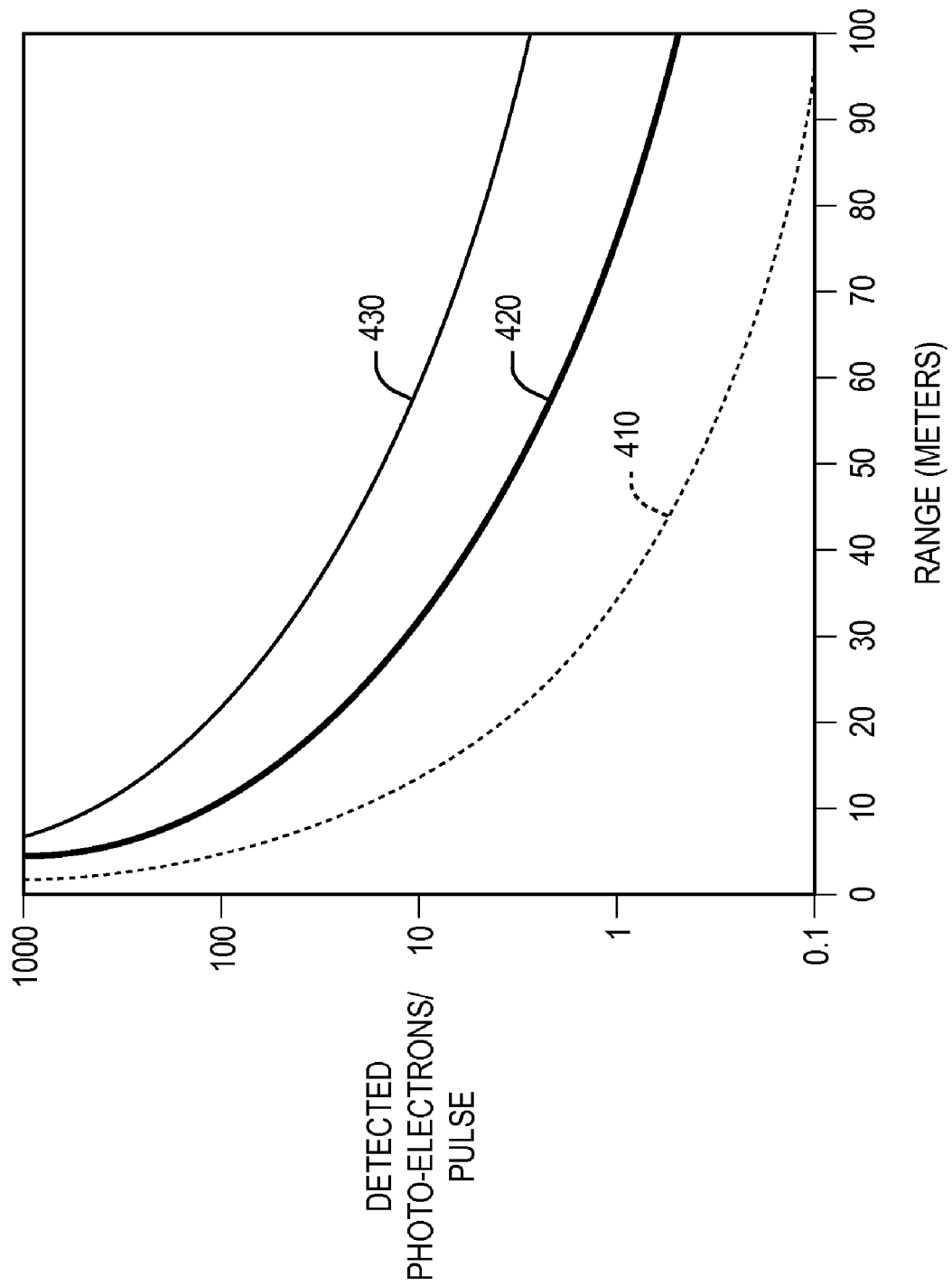
FIG. 4 presents a graph of detected photo-electrons/pulse as a function of standoff range for various values of laser power, in accord with embodiments of the invention.

Some embodiments of the present invention are directed to standoff detection where the distance between the fluorescing sample and detector can be on the order of tens of meters or larger. Such distances can be possible in light of the data presented in the Examples, and based upon calculations herein. For instance, in a single pulse system, the received fluorescence signal from a sample can be modeled as:

$$\text{Signal} = \frac{FP_L \exp(-2\alpha R) \sigma T Q_E A_o}{\pi R^2}$$

where F is a fill factor (F=1 assumes each photon interacts with an explosive molecule), $P_L$ is the laser power, $\alpha$ is the atmospheric absorption coefficient ($2 \times 10^{-3}$/m), R is the range to target, $\sigma$ is the effective cross section of a molecule to be detected (fluence-dependent), T is the optical transmission, $Q_E$ is the detector quantum efficiency, and Ao is the collection optics area. Assuming a 1 kHz, 2 nsec laser illuminating a 1 cm$^2$ area (F=1), and T=0.06, $Q_E$=0.3, Ao=30 cm, and parameters consistent with TNT as a material to be detected, the performance is as shown in FIG. 4, in which detected photoelectrons/pulse are displayed as a function of R (in meters) for various transmitted laser powers. In particular, graphs 410, 420, 430 correspond to laser powers of 2.5 watts, 5 watts, and 10 watts, respectively.

As the background signal is expected to be quite low, detection is assumed to be limited by the Poisson statistics of the signal itself. As such, a signal-to-noise ratio of 10 is predicted for a signal level of 100 photoelectrons. Assuming an operational signal-to-noise ratio of 10 thus yields detection ranges in the range of tens of meters depending on laser power. Other variations in parameters can result in an extension of standoff range. For instance, the 10 W laser eye-safe limit need not be imposed. Accordingly, a higher power laser can extend the standoff detection range.

EXAMPLES

The following examples are provided to illustrate some embodiments of the invention. The examples are not intended to limit the scope of any particular embodiment(s) utilized.

Close Range Measurements

Measurements were performed in a number of detection geometries. The physics of the detection process did not change substantially in any of these configurations. The close-range configuration, depicted in FIG. 5, utilized a tunable laser focused onto the samples from the side at an incident angle of ~60° from normal. Samples were placed on ultraviolet (UV) grade fused silica substrates. A solar-blind photomultiplier tube (PMT) with narrowband filters was positioned 6 cm directly above the sample, and used as the detector. The laser was a Continuum 9030 system, which frequency-triples a Nd:YAG source, inputting the 355 nm result into an optical parametric oscillator (OPO) providing frequency selectivity. The output of the OPO was subsequently doubled, providing variable laser output from 215 to 310 nm. All wavelengths used in these examples were in air. The laser output was a ~1 cm$^2$ beam of 30 Hz pulses with energies of 2-3 mJ per pulse and pulse widths of ~7 ns. The laser linewidth was 0.03-0.04 nm near the wavelengths of interest. The beam was focused to ~0.1 cm$^2$ at the sample using a convex UV lens. The output laser wavelengths were confirmed using an Ocean Optics spectrometer, which was calibrated with a Hg lamp. All wavelengths reported are in air. The spot size was estimated by exposing a photoresist to the UV illumination at the sample location and measuring the resultant spot. In situ measurements of the laser power were recorded using a Molectron power meter and pyrometer-based measurement head; laser power fluctuations during a typical measurement were approximately 10%. The PMT was a Perkin Elmer Cs—Te channel photomultiplier with measured dark counts of ~4 per minute, single-photon sensitivity, and quantum efficiency of 10% near the signals of interest (220-230 nm). The PMT signal was amplified using a 5 kHz preamplifier; the resulting signal was recorded using an A/D converter and computer.

Narrowband filters were used to suppress the scattered laser light. The filters were fused silica substrates with a dielectric film stack coating designed by Barr Associates. The total transmission of the three-filter stack used in these measurements was 0.3% (OD 2.5) at the signal wavelength of 226 nm, and OD 11 at the primary laser wavelength of 236 nm, providing a rejection ratio of nearly nine orders of magnitude between the laser and the expected signal.

For the close-range detection geometry, the following estimates can be made regarding signal collection efficiency. Assuming the signal fluoresces in a Lambertian manner, and using the 0.3% transmission at the signal wavelength of 226 nm, the 0.25" detector aperture, the detection range of 6 cm, and quantum efficiency of 10%, we estimate a collection efficiency of $4 \times 10^{-7}$ of all emitted signal photons. Noting that there are $10^{15}$ photons per mJ at these wavelengths, we would expect to collect $4 \times 10^8$ photons per mJ of signal photons.

A variety of explosives in a variety of morphologies were studied. The explosives included 2,6-dinitrotoluene (DNT), TNT, pentaerythritol tetranitrate (PETN), and cyclotrimethylenetrinitramine (RDX). DNT, as received from Aldrich, took the form of small granules roughly the size of salt crystals. Studies were performed on mounds of these solid granules, in addition to a liquid form which was obtained by heating the granules to 80° C. With the exception of the liquid DNT measurements, all other measurements were performed at room temperature under ambient atmospheric conditions. Military-grade TNT was studied in a solid pellet form. It was also studied in the form of a trace coating on sand particles (8% TNT by weight). Additionally, it was dropcast from a dilute acetone solution to form a thin film containing a calibrated amount (1 μg) of TNT residue. Military-grade PETN was studied in the form of a white powder. RDX was studied both as a trace coating on sand (8% by weight) and as the dominant component in the putty-like C4 plastic explosive. In all morphologies, the experimentally observed signal remained essentially the same, with only variations in the signal magnitude.

Results: Bulk Detection

Figure 6:
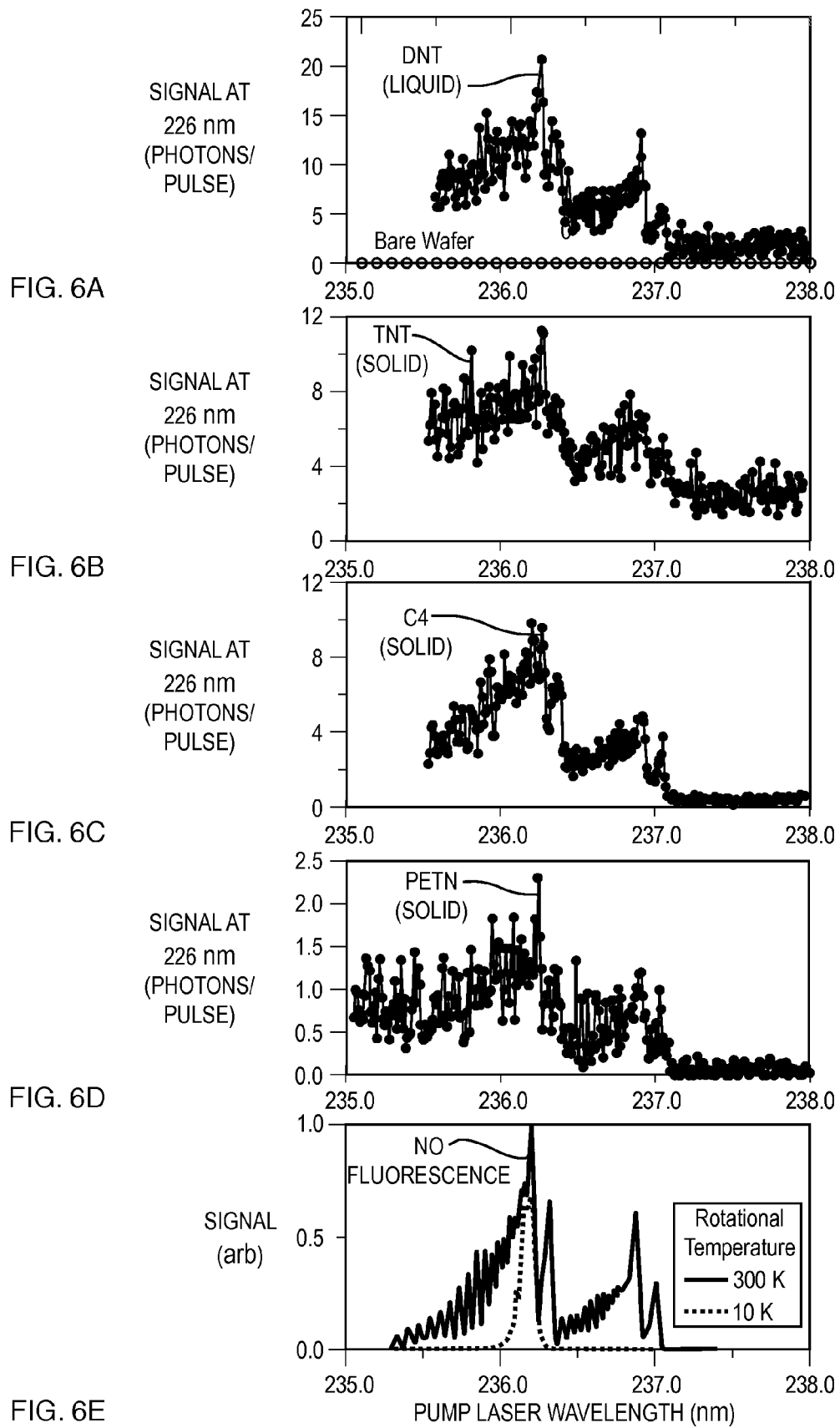
FIG. 6 presents measurement data showing of the number of photons at 226 nm per excitation pulse detected as a function of excitation wavelength for various explosive materials, and a plot of calculated NO fluorescence signal as a function of excitation wavelength for different rotational temperatures, consistent with some embodiments of the invention.

FIG. 6 displays the results of close-range detection measurements of DNT, TNT, C4 (RDX active component), and PETN. All samples were in bulk quantities. For these measurements, the incident laser was scanned from 235 to 238 nm with 0.01 nm steps. Data were taken at the eye and skin safe fluence of 10 mJ/cm$^2$ (1 mJ pulses over 0.1 cm$^2$ area). Data points represent 6 pulse averages, with the exception of the background measurements on the bare silica wafer for which the data points are 60 pulse averages. The measured background scatter (open circles in top graph) from the bare silica substrate followed the steep slope of the interference filter with a signal of less than 0.1 photon per pulse (~0.03 photons) at 236.2 nm. All explosive samples display the same multi-peak structure with a maximum signal at 236.2 nm and shoulder near 236.3 nm. They also display a secondary peak at 236.9 nm, again with accompanying shoulder. It is of note that the vapor pressures for these compounds differ by almost six orders of magnitude (DNT vapor pressure ~ppm; RDX vapor pressure ~ppt) while their signal strengths are within an order of magnitude, indicating that the observed signal is not related to the ambient vapors of the materials, but rather the condensed phase itself.

The bottom graph of FIG. 6 displays the predicted fluorescence of NO assuming excitation from the first vibrationally excited state (v"=1) of its electronic ground state ($X^2\Pi$) to the vibrational ground state (v"=0) of its first electronically excited state ($A^2\Sigma^+$); two different rotational temperatures are displayed. These results were obtained using the LIFBASE software package (J. Luque and D. R. Crosley, "LIFBASE: Database and Spectral Simulation Program," SRI International Report MP 99-009 (1999); J. Luque and D. R. Crosley, J. Chem. Phys., 111, 7405 (1999)) and assumed a linewidth of 0.03 nm. Comparison of the experimental data to the NO spectrum provides clear evidence that the measured signal is indeed being generated by an excited NO species. The detailed structure evident in the data is due to the rotational fine structure of the excited NO. The data near v"=1 fit the predicted NO fluorescence well for a rotational temperature of 1000° K. Regardless of the specifics of the rotational temperature, the peak signal is always observed at 236.2 nm with a linewidth of several tenths of a nanometer. Accordingly, a laser tuned to these frequencies can be used to detect these compounds.

Figure 7:
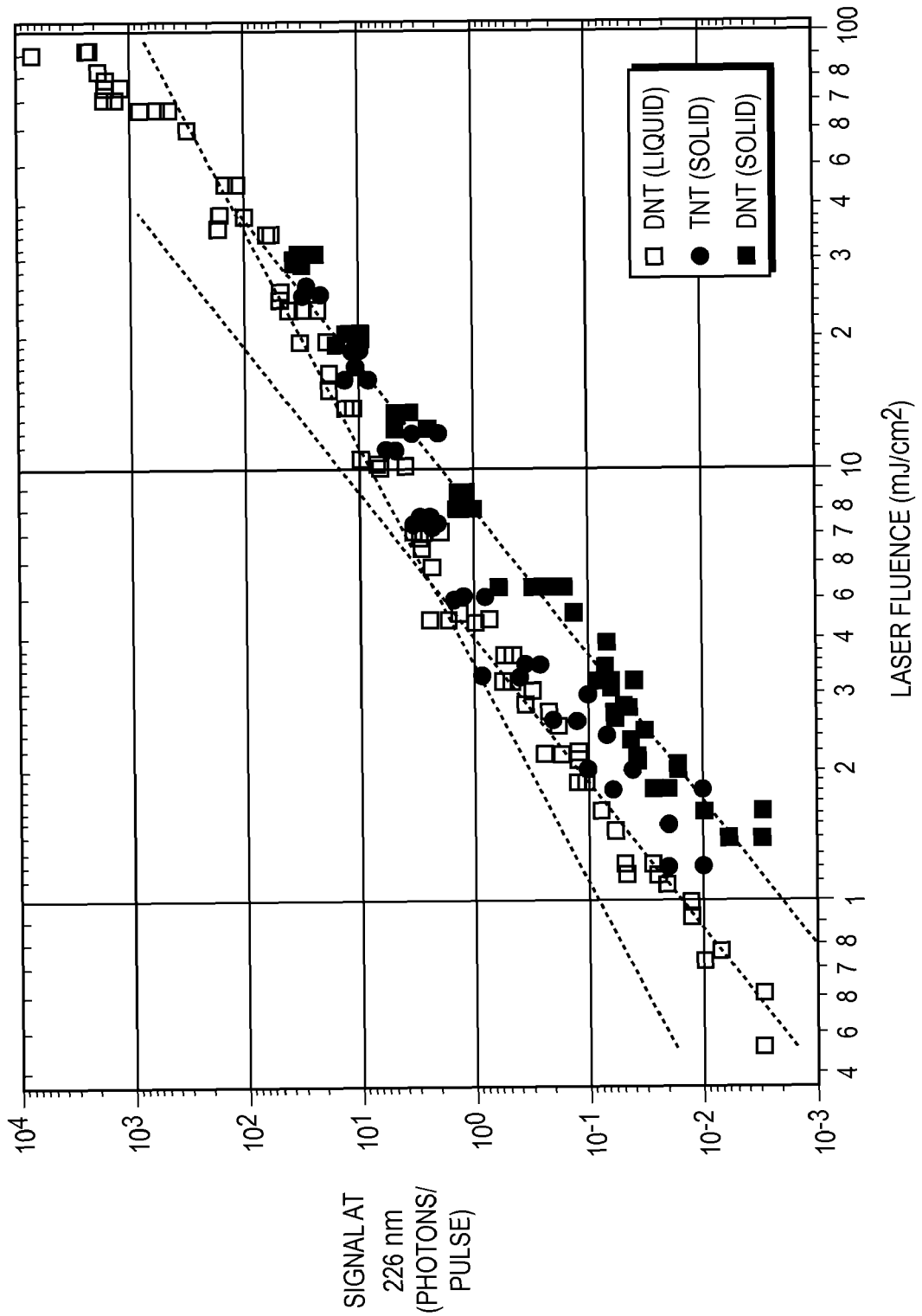
FIG. 7 presents measurement data showing number of photons at 226 nm per laser pulse at 236.2 nm detected as a function of laser fluence for DNT and TNT, consistent with some aspects of the invention.

Since the fluorescence technique involves multiple excitation photons (at least one photon for dissociation and vaporization, and one photon for excitation), a nonlinear dependence of the fluorescence signal on the laser fluence is expected. FIG. 7 displays the fluorescence signal as a function of laser fluence for DNT and TNT at the fixed laser wavelength of 236.2 nm. Data were collected using a spot size of = 0.1 $cm^2$. Data points are averages over a number of samples, the amount of which depended upon the signal strength. In order to ensure no systematic drift affected the measurements, the fluence was decreased to its minimum and then subsequently increased. No significant deviations were observed. Several fluence dependencies were observed, dependent on the material, its physical phase (solid or liquid) and the laser wavelength. For laser irradiation at 236.2 nm, both liquid DNT and solid TNT show similar behavior in which there appears to be a cubic dependence at low laser fluences crossing over to a quadratic dependence at higher fluences. At very high fluences (>60 mJ/$cm^2$), DNT displays a systematic shift by roughly a factor of two above its quadratic behavior below 60 mJ/$cm^2$. In contrast, cubic dependence on fluence is observed in solid DNT or DNT in which the v"=2 state is being probed (246.9 nm, 242 nm, not shown in FIG. 7).

Figure 8:
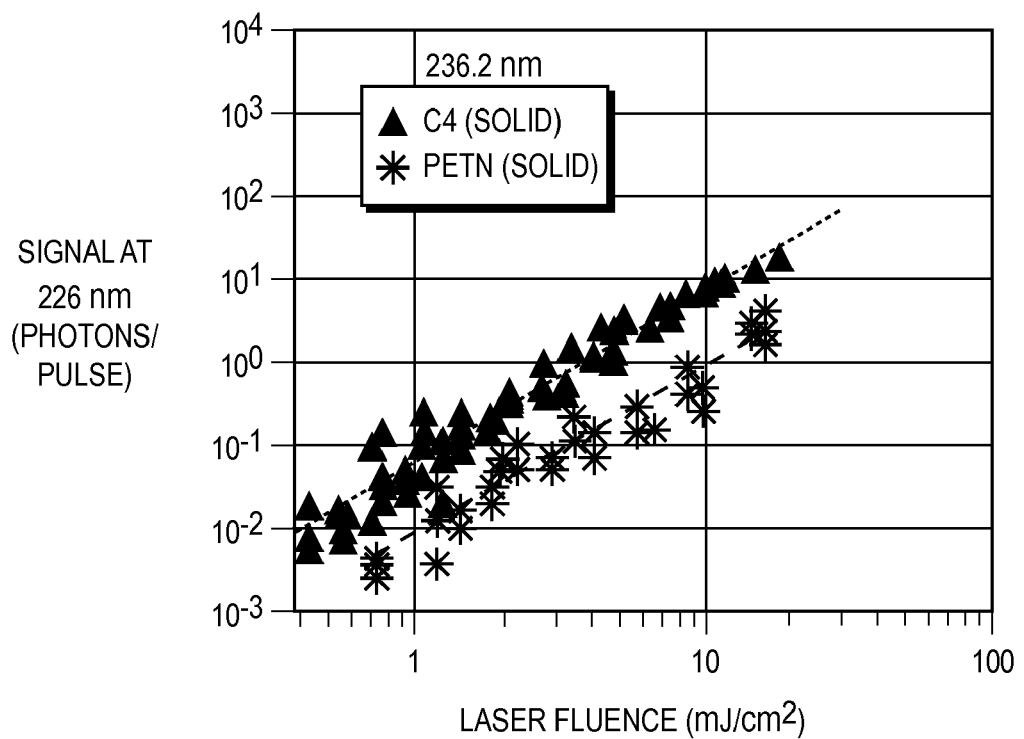
FIG. 8 presents measurement data showing number of photons at 226 nm per laser pulse at 236.2 nm detected as a function of laser fluence for C4 and PETN, consistent with some aspects of the invention.

Similar data were generated for C4 and PETN as shown in FIG. 8. Both C4 (active component being RDX) and PETN display quadratic dependencies on laser fluence over the full range of our experimental conditions.

Other properties, in addition to the peak fluorescence signal, were observed to vary with laser fluence. Photo-ablation rates at 236.2 nm were measured by counting the number of pulses required to ablate a thin film of known thickness. For DNT, ablation rates of 23 nm/pulse (28 mJ/$cm^2$) and 4 nm/pulse (5 mJ/$cm^2$) were estimated. For TNT, an ablation rate of 28 nm/pulse (25 mJ/$cm^2$) was estimated.

Results: Trace Detection

Detection of explosives in morphologies other than bulk form was also demonstrated. TNT and RDX on sand (8% by mass) were studied with results very similar to those above. Generally, the overall signal level was approximately twice as large as those above, likely due to the greater surface area provided by the sand matrix. Trace level detection was also demonstrated using calibrated quantities of explosives dissolved in acetone. These were dropcast on silicon wafers to yield concentrations of 2 μg/$cm^2$. Both RDX and TNT were investigated in this manner yielding signals roughly half of those reported for the bulk materials.

Figure 9:
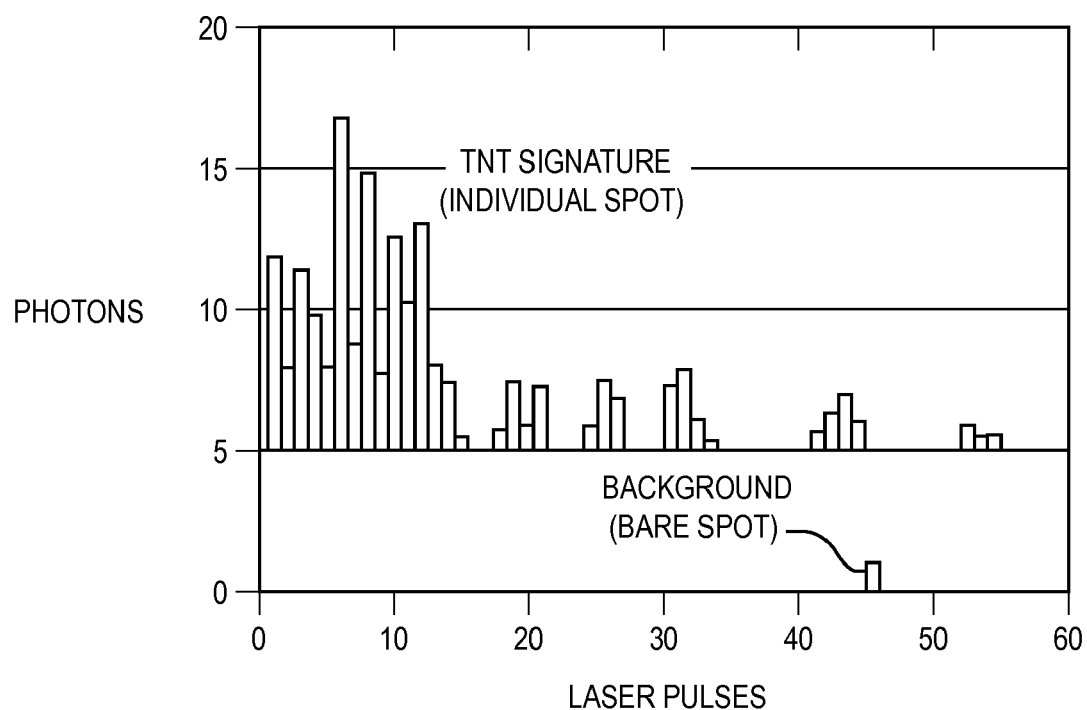
FIG. 9 presents a bar graph of photons detected as a function of number of laser pulses for exciting a TNT sample, in accord with some embodiments of the invention.

For laser fluences of 10 mJ/$cm^2$ and a wavelength of 236.2 μm, complete ablation takes about 20 laser pulses using a spot size of about 0.1 $cm^2$. FIG. 9 displays a time series of the TNT signal as a function of laser pulses. Photoablation rates of TNT at 236.2 nm were measured by counting the number of pulses required to ablate a thin film of known thickness. An ablation rate of 28 nm/pulse (at 25 mJ/$cm^2$) was estimated. Thus, we estimate that the average TNT thickness is 560 nm. Optical images of the film indicate coverage and thickness that are highly non-uniform. Also displayed in FIG. 9 is the photo-response from the bare silicon wafer, which is significantly weaker than that of the TNT.

Remote Measurements

Figure 10:
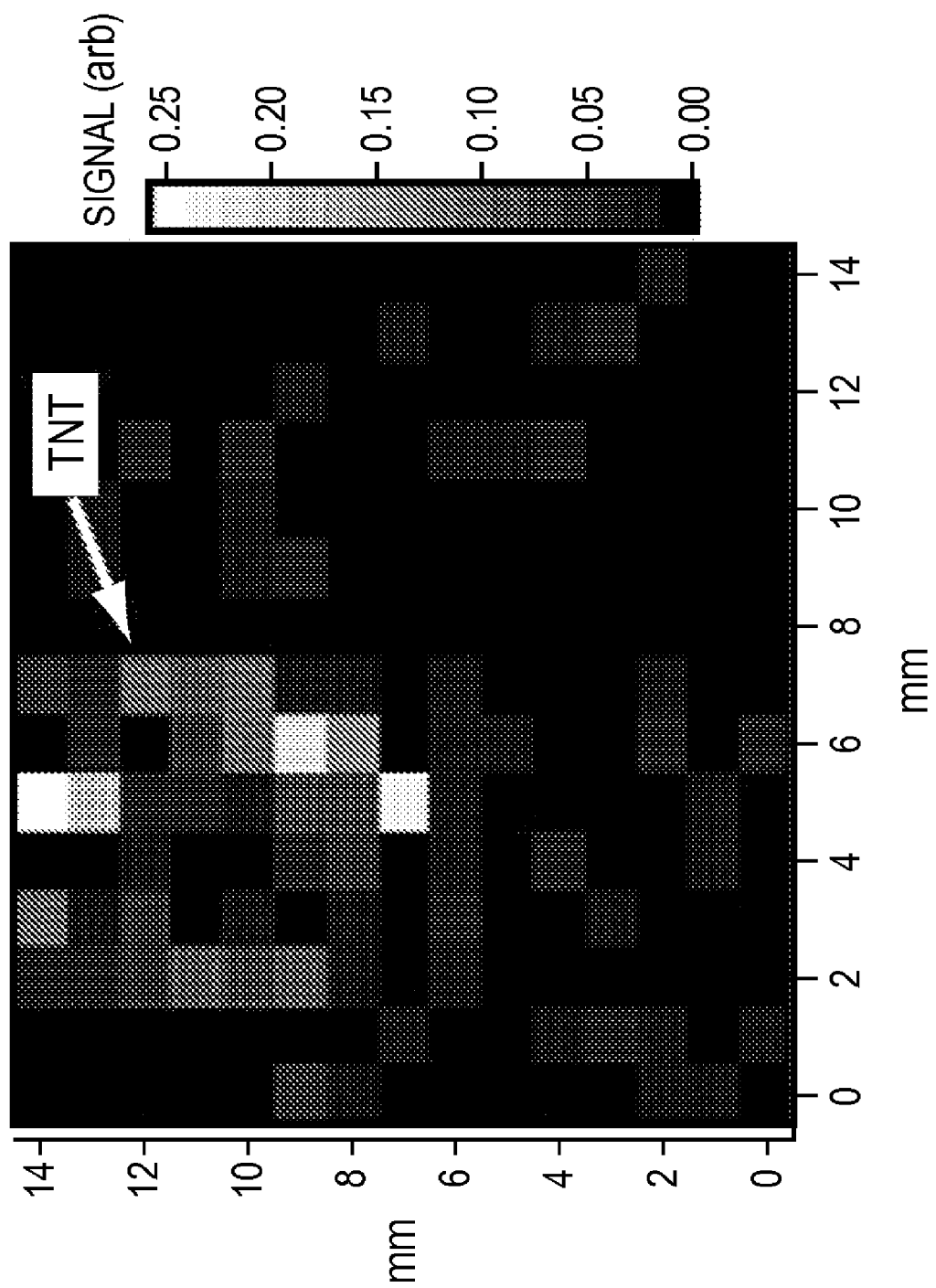
FIG. 10 presents an image of the signal received as a function of spatial position for the fluorescence of a TNT sample from a remote measurement, consistent with some aspects of the invention.

Detection at ranges of 3.3 meters were achieved via the use of 2 inch diameter collection optics placed in front of the PMT detector. Bulk TNT was placed on double sticky tape. The surface was scanned in a raster pattern, with the resulting image shown in FIG. 10. The TNT has a clearly stronger signal than the background substrate. The laser beam and detector were aligned facing the sample from the same direction, with the detector at a distance of 3.3 m from the sample and the laser at roughly 10 m from the sample.

Clutter Measurements

Figure 11:
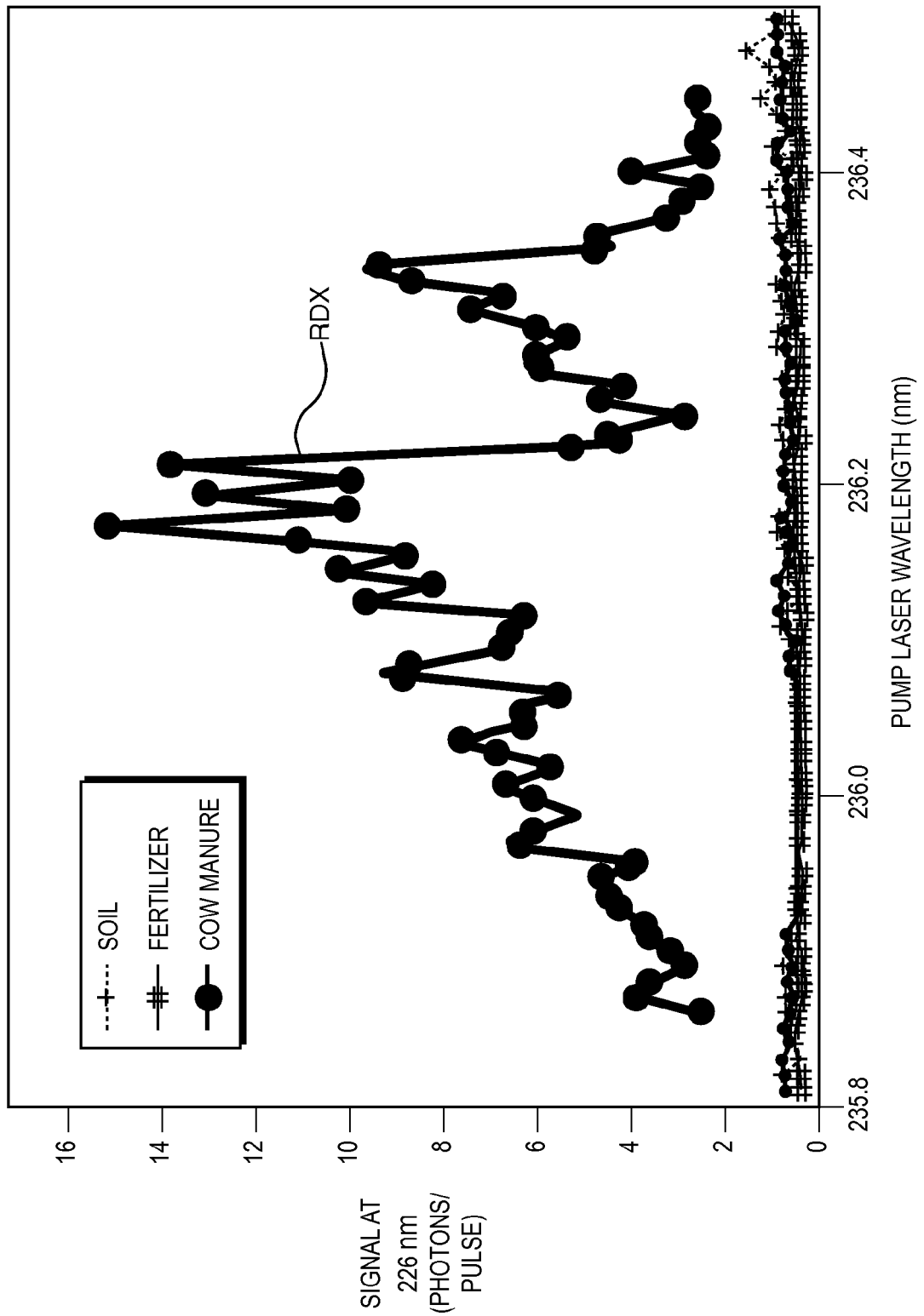
FIG. 11 presents measurement data showing number of photons at 226 nm per excitation pulse detected as a function of excitation wavelength for RDX, soil, fertilizer, and cow manure, consistent with some aspects of the invention.

Since excited NO is the indicator used to identify the explosives, non-explosive sources of excited NO have the potential to form significant false alarms. Measurements of inorganic nitrates and materials containing inorganic nitrates were conducted to determine whether they produce excited NO. The measurements were performed in the close-range configuration at a fluence of 10 mJ/$cm^2$ (1 mJ over 0.1 $cm^2$). The materials included potting soil, fertilizer, cow manure, $KNO_3$, $AgNO_3$, and $NaNO_2$. As shown in FIG. 11, none showed any evidence of excited NO.

Urea Nitrate Measurements

Figure 5:
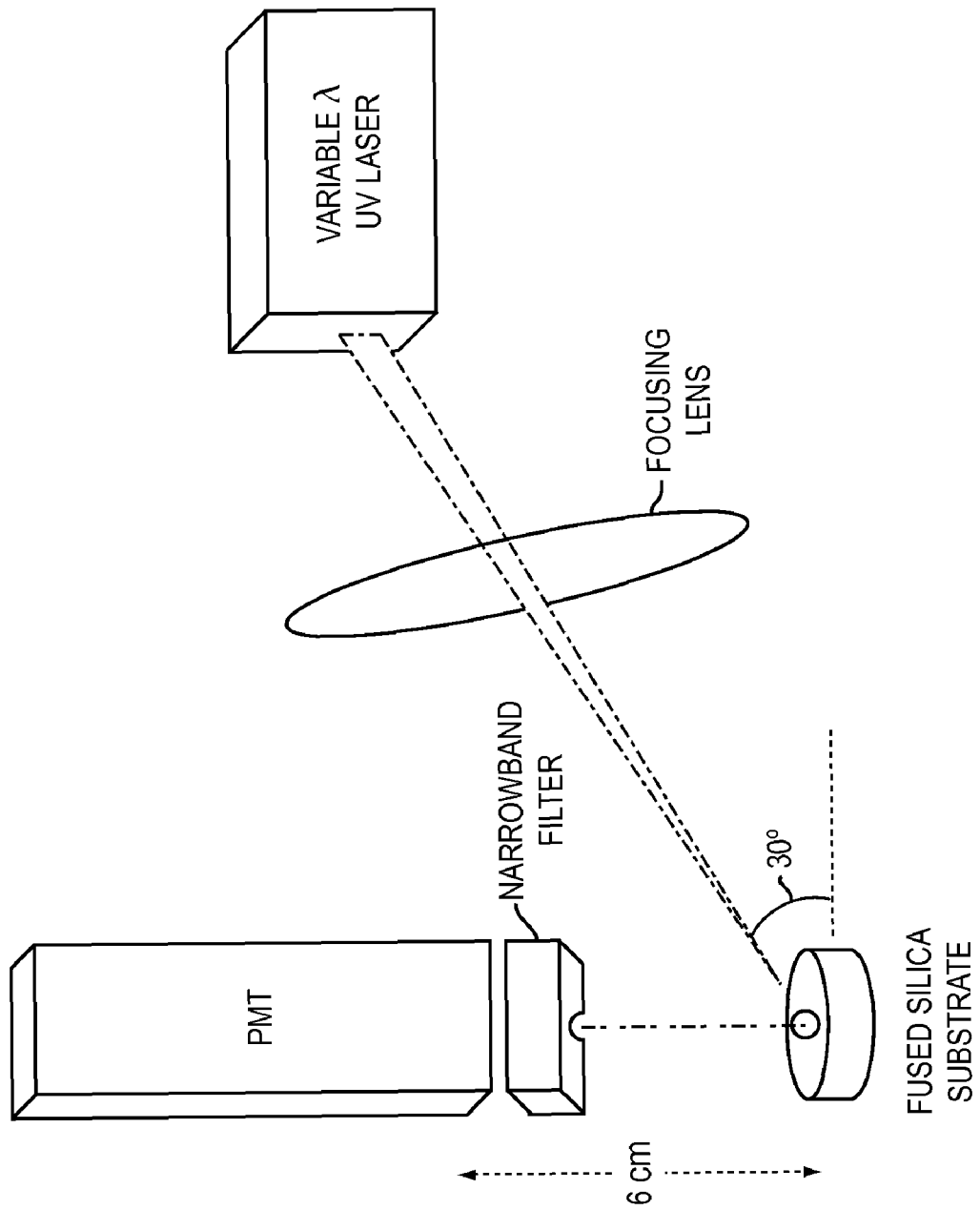
FIG. 5 presents a schematic diagram of the system used to perform close range measurements, consistent with some aspects of the invention.
Figure 12A:
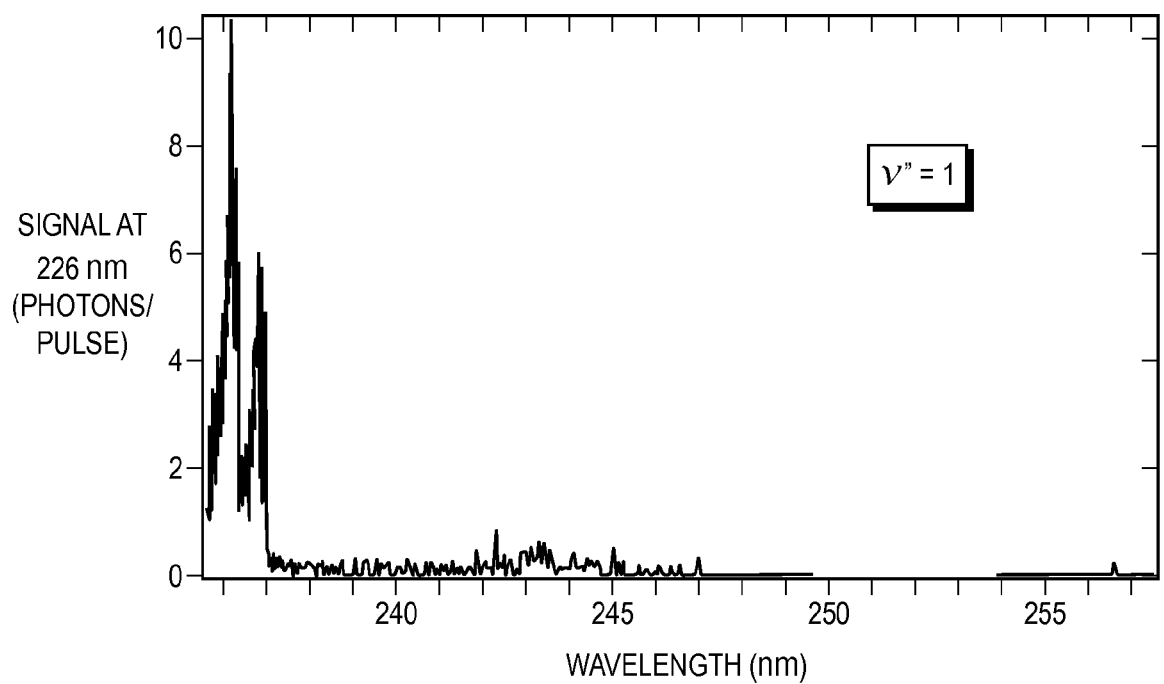
FIG. 12A presents measurement data showing of the number of photons at 226 nm per excitation pulse detected as a function of excitation wavelength for a sample of solid urea nitrate, consistent with some embodiments of the invention.

The system described with respect to FIG. 5, to make close range measurements, was utilized to measure the fluorescence signal from a bulk sample of ground solid urea nitrate pellets. The system provided about 20 mJ/$cm^2$ of energy to the sample at the excitation wavelength under examination. FIG. 12A shows the 226 nm signal strength detected (photons/pulse) as a function of excitation wavelength from about 235 nm to about 260 nm. Similar to the results discussed for various explosive samples shown in FIG. 6, the photo-induced dissociation and laser-induced fluorescence of the urea nitrate sample showed a signal appearing to correspond to formation of NO fragments in the first vibrationally excited state (v"=1) of the electronic ground state.

Figure 12B:
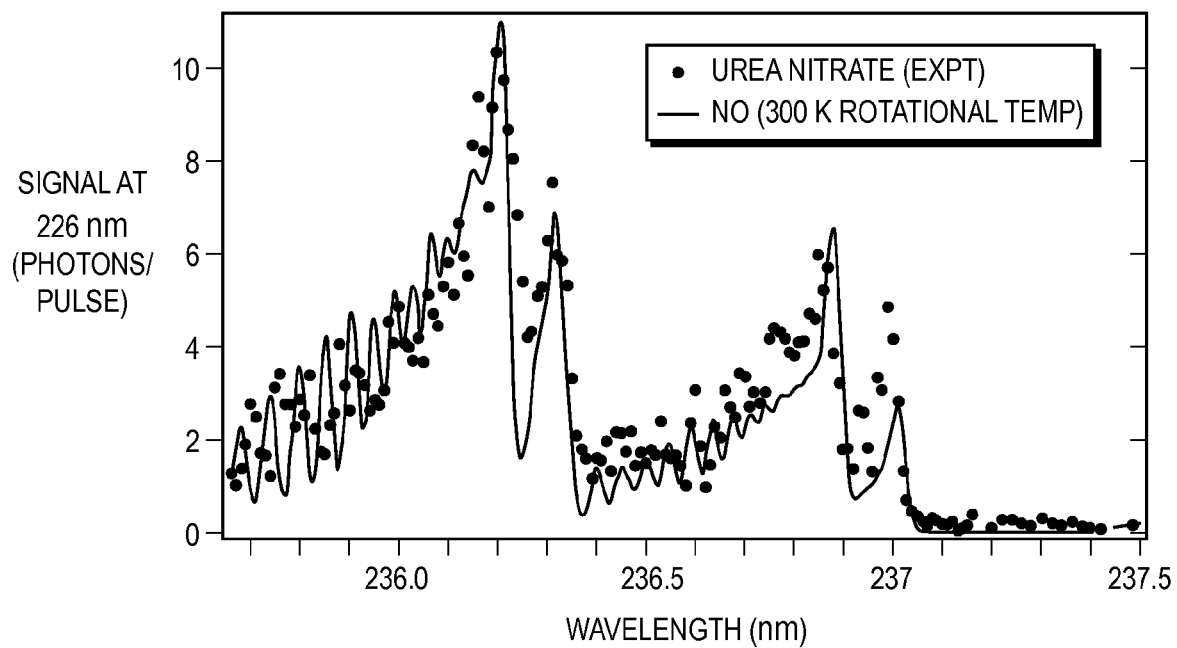
FIG. 12B presents measurement data of FIG. 12A for a range of excitation wavelengths from about 235 nm to about 237.5 nm overlaid with a calculation for a NO fragment at a rotational temperature of 300° K.

This is confirmed by the results shown in FIG. 12B, which reproduce the data from FIG. 12A for the excitation wavelength range of about 235 nm to about 237.5 nm. Overlaid on the experimental results of FIG. 12B is a calculation for the 226 nm fluorescence of a NO fragment at a rotational temperature of 300° K over the same excitation wavelengths. The agreement between the data and the calculation further strengthen the belief that NO fragment excitation and relaxation are being observed from the urea nitrate sample. The signal strength for the urea nitrate sample was comparable to the signal strength measured for a solid DNT sample.

EQUIVALENTS

While the present invention has been described in terms of specific methods, structures, and devices it is understood that variations and modifications will occur to those skilled in the art upon consideration of the present invention. As well, the features illustrated or described in connection with one embodiment can be combined with the features of other embodiments. Such modifications and variations are intended to be included within the scope of the present invention. Those skilled in the art will appreciate, or be able to ascertain using no more than routine experimentation, further features and advantages of the invention based on the above-described embodiments. Accordingly, the invention is not necessarily to be limited by what has been particularly shown and described.

All publications and references are herein expressly incorporated by reference in their entirety. The terms "a" and "an" can be used interchangeably, and are equivalent to the phrase "one or more" as utilized in the present application. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise specifically claimed. No language in the specification should be construed as indicating any non-claimed element as essential to the practice of the invention.

What is claimed is:

1. A method for identifying a presence of a substance in an unknown sample, comprising:
   photodissociating the sample into one or more portions including a NO molecule, the NO molecule having an electron in a first-vibrational excited state of an electronic ground state;
   employing laser-induced fluorescence to induce fluorescence of the NO molecule; and
   detecting the florescence of the NO molecule to thereby identify the presence of the substance.

2. The method of claim 1, wherein the step of photodissociating comprises photodissociating the sample into a plurality of NO molecules each NO molecule having an electron in a first-vibrational excited state and a distinct rotational state, and further wherein the step of employing laser-induced fluorescence includes inducing fluorescence of the NO molecules in distinct rotational states.

3. The method of claim 1, wherein the step of detecting comprises distinguishing the substance from a presence of at least one material containing a NO portion.

4. The method of claim 3, wherein at least one material containing a NO portion is at least one of an atmospheric NO-containing compound, an inorganic NO-containing compound, an inorganic nitrate, and fertilizer.

5. The method of claim 1, wherein the substance comprises a portion of an explosive compound.

6. The method of claim 5, wherein the explosive compound comprises at least one of 2,6-dinitrotoluene, 2,4,6 trinitrotoluene, pentaerythritol tetranitrate, hexahydro-1,3,5-trinitro-1,3,5-triazine, and cyclotrimethylenetrinitramine.

7. The method of claim 1, wherein the step of photodissociating the sample comprises photodissociating a solid material.

8. The method of claim 1, wherein the step of photodissociating the sample comprises exposing the sample to a wavelength of light that differs from a wavelength of light used for employing laser-induced fluorescence.

9. The method of claim 1, wherein the steps of photodissociating and employing laser-induced fluorescence are performed using light energy from a single source.

10. The method of claim 1, wherein the step of employing laser-induced fluorescence comprises exciting the NO molecule using light having a wavelength of about 236.2 nm.

11. The method of claim 1, wherein the method is employed in a stand-off mode.

12. The method of claim 11, wherein the step of detecting the fluorescence comprises collecting the fluorescence using a detector positioned at least about 50 cm from the sample.

13. The method of claim 1, wherein the substance comprises urea nitrate.

14. The method of claim 1, wherein the step of detecting comprises detecting fluorescence at a wavelength of about 226 nm.

15. The method of claim 1, wherein the method is carried out in ambient conditions.

16. A method for identifying a presence of a substance in an unknown solid sample, comprising:
   photodissociating the solid sample into one or more portions including a NO molecule;
   employing laser-induced fluorescence to induce fluorescence of the NO molecule; and
   detecting the florescence of the NO molecule to thereby identify the presence of the substance.

17. The method of claim 16, wherein the NO molecule has an electron in a first-vibrational excited state of an electronic ground state.

* * * * *